(12) United States Patent
Toshimitsu et al.

(10) Patent No.: US 8,574,621 B2
(45) Date of Patent: Nov. 5, 2013

(54) ADHESIVE PATCH FOR TREATMENT OF TINEA UNGUIUM

(75) Inventors: Arata Toshimitsu, Tsukuba (JP); Naoko Fujita, Tsukuba (JP); Toshihiro Kogure, Tsukuba (JP)

(73) Assignee: Hisamitsu Pharmaceutical Co., Inc., Tosu-Shi, Saga (JP)

( * ) Notice: Subject to any disclaimer, the term of this patent is extended or adjusted under 35 U.S.C. 154(b) by 0 days.

(21) Appl. No.: 13/577,110

(22) PCT Filed: Feb. 7, 2011

(86) PCT No.: PCT/JP2011/052550
§ 371 (c)(1),
(2), (4) Date: Aug. 3, 2012

(87) PCT Pub. No.: WO2011/096566
PCT Pub. Date: Aug. 11, 2011

(65) Prior Publication Data
US 2012/0302644 A1     Nov. 29, 2012

(30) Foreign Application Priority Data
Feb. 5, 2010   (JP) ................................ P2010-024533

(51) Int. Cl.
*A61F 13/02*   (2006.01)
*A61K 31/135*  (2006.01)
(52) U.S. Cl.
USPC ......................................... 424/448; 514/655
(58) Field of Classification Search
None
See application file for complete search history.

(56) References Cited

U.S. PATENT DOCUMENTS

2009/0324696 A1 *  12/2009  Toshimitsu et al. ........... 424/448

FOREIGN PATENT DOCUMENTS

| JP | 9-504536 A | 5/1997 |
| JP | 10-330247 A | 12/1998 |
| JP | 2003-525641 A | 9/2003 |
| JP | 2005-501885 A | 1/2005 |
| WO | 2008/026381 A1 | 3/2008 |
| WO | 2008/102880 A1 | 8/2008 |
| WO | 2008/105038 A1 | 9/2008 |

OTHER PUBLICATIONS

International Preliminary Report on Patentability for International Patent Application No. PCT/JP2011/052550; mailed on Sep. 27, 2012.

* cited by examiner

*Primary Examiner* — Jeffrey S. Lundgren
*Assistant Examiner* — Tori M Strong
(74) *Attorney, Agent, or Firm* — Nath, Goldberg & Meyer; Sheldon M. McGee

(57) ABSTRACT

The present invention provides an adhesive patch for the treatment of tinea unguium intended to be applied once a day, comprising terbinafine and/or a pharmacologically acceptable salt thereof in an amount of 3 mg/cm$^2$, wherein the adhesive patch is used so that the terbinafine concentration in nails may be 295±127 ng/mg and the terbinafine concentration in plasma may be 23 pg/mL or less, 8 weeks after the start of application, per cm$^2$ of the patch size.

3 Claims, 1 Drawing Sheet

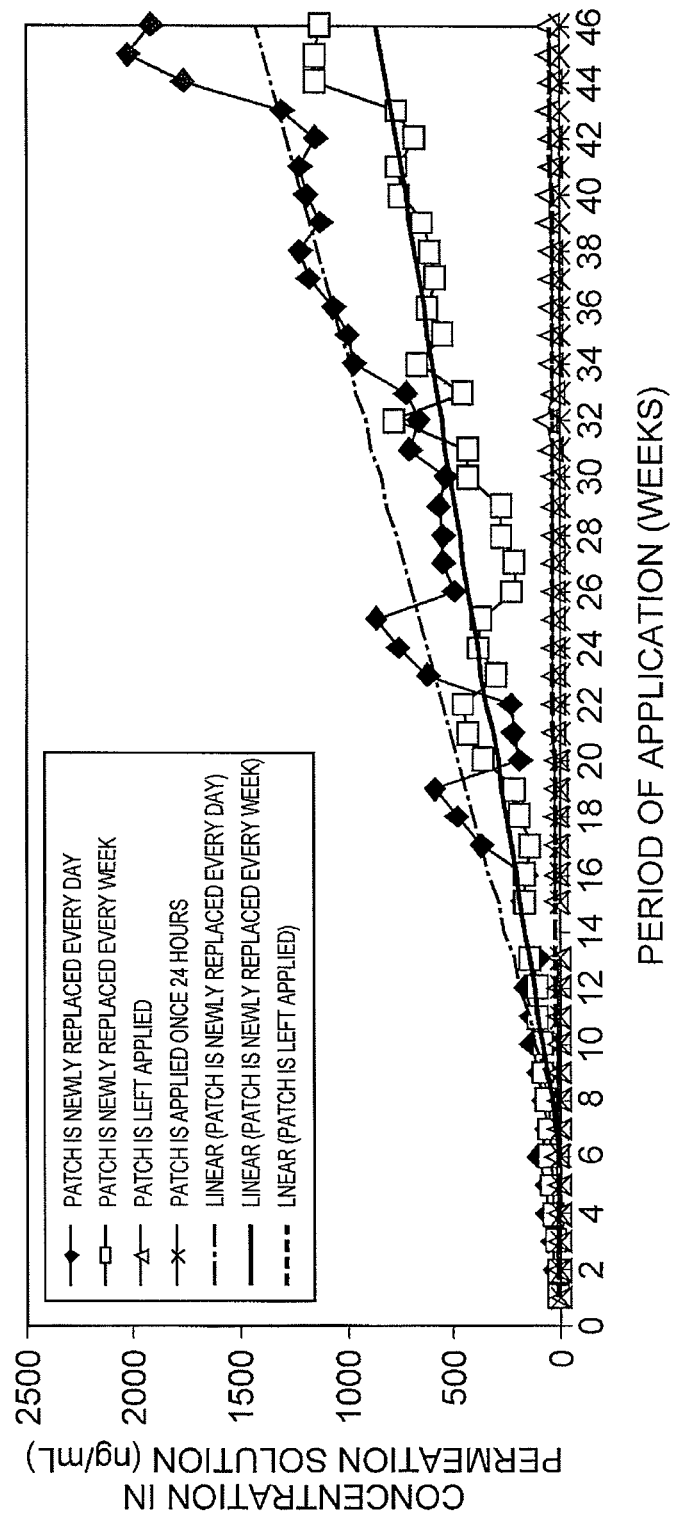

ADHESIVE PATCH FOR TREATMENT OF TINEA UNGUIUM

TECHNICAL FIELD

The present invention relates to an adhesive patch for the treatment of tinea unguium.

BACKGROUND ART

Terbinafine is known as an effective antifungal agent belonging to the allylamine family and is used for the treatment of tinea unguium. Tinea unguium is an intractable disease caused by the intrusion of Trichophyton into nails and is characterized by conditions such as cloudiness, thickening, and deformation of a nail surface.

At present, oral administration of antifungal agents such as terbinafine or itraconazole belonging to the triazole family on a long-term basis is the mainstream treatment of tinea unguium, but it has problems such as critical side effects, such as hepatopathy caused by taking antifungal agents for a long period of time, and an interaction with other agents. It is reported that, generally, the dose of the oral formulation of terbinafine is 125 mg/day (to be taken once a day after a meal) for an adult; the terbinafine concentration in plasma reaches a steady state in 10 weeks and is 280 ng/mL in average; and the terbinafine concentration in nails reaches a steady state in 12 weeks and is 0.78 ng/mg in average.

On the other hand, several external preparations for nails in which an antifungal agent is mixed have been proposed because it is expected that the external preparations for nails have low drug permeation into plasma and can reduce the side effects of the antifungal agent and that the high concentration of the drug in nails can be more easily achieved than an oral agent. However, since a sufficient permeation amount of the drug into nails having high barrier ability cannot be obtained, these external preparations not necessarily have a high therapeutic effect under the present circumstances.

Further, an adhesive patch containing an antifungal agent has also been proposed from the point that administration is convenient (Patent Literatures 1 to 4). In the case of these adhesive patches, the use feeling is improved compared with the external preparations which are not adhesive patches such as liquid formulations, and the drug permeability into nails is improved because direct application to nails allows the drug to sustainingly act on the nails; but a permeation amount of the drug sufficient for the treatment of tinea unguium is not yet achieved. Furthermore, an attempt to effectively permeate a drug into nails has been performed in recent years by mixing terbinafine at a high concentration in a pressure sensitive adhesive of an adhesive patch (Patent Literatures 5 to 7).

CITATION LIST

Patent Literature

Patent Literature 1: Japanese Patent Application Laid-Open No. 10-330247
Patent Literature 2: National Publication of International Patent Application No. 2003-525641
Patent Literature 3: National Publication of International Patent Application No. 09-504536
Patent Literature 4: National Publication of International Patent Application No. 2005-501885
Patent Literature 5: International Publication No. WO 2008/026381
Patent Literature 6: International Publication No. WO 2008/102880
Patent Literature 7: International Publication No. WO 2008/105038

SUMMARY OF INVENTION

Problems to be Solved by the Invention

In Patent Literatures 5 to 7, it is shown that the permeability of terbinafine into nails is improved and that a high terbinafine concentration in nails can be achieved, in the in vitro study, by mixing terbinafine at a high concentration in the pressure sensitive adhesive layer of an adhesive patch.

However, since these techniques use terbinafine at a high concentration, it is unknown that when actually administered to human nails, the side effects caused by terbinafine can be sufficiently reduced or not, and so an adhesive patch that can sufficiently reduce side effects is required. Furthermore, these techniques pose the problem of high cost because a large amount of terbinafine is used. Thus, an adhesive patch that can efficiently use terbinafine is required.

The present invention has been made in view of such circumstances, and an object of the present invention is to provide a terbinafine-containing adhesive patch for the treatment of tinea unguium that can efficiently exhibit the effect of terbinafine and can sufficiently reduce side effects, in the treatment of tinea unguium.

Means for Solving the Problems

The present inventors have found that the terbinafine concentration in nails and the terbinafine concentration in plasma can be made to reach a predetermined concentration within a predetermined period of time by allowing a predetermined amount of terbinafine and/or a pharmacologically acceptable salt thereof to be contained per a definite size of an adhesive patch and administering it to human nails by a predetermined administration method; and that terbinafine can be efficiently used because such an adhesive patch can maintain the terbinafine concentration in nails at a steady state after a predetermined lapse of period. The present inventors have also found that side effects can be reduced as much as possible by suppressing the terbinafine concentration in plasma to an extremely low concentration. The present invention is based on these findings.

Specifically, the present invention provides an adhesive patch for the treatment of tinea unguium intended to be applied once a day, comprising terbinafine and/or a pharmacologically acceptable salt thereof in an amount of 3 mg/cm$^2$, wherein the adhesive patch is used so that a terbinafine concentration in nails may be 295±127 ng/mg and a terbinafine concentration in plasma may be 23 pg/mL or less, 8 weeks after the start of application, per cm$^2$ of the patch size.

According to the adhesive patch for the treatment of tinea unguium of the present invention, a sufficient terbinafine permeability to nails is obtained and a high-concentration terbinafine can be administered to nails by employing the above constitution, and on the other hand, the transfer into blood can be reduced to an extremely low level. Therefore, side effects are extremely lowered, and the amount of terbinafine used can be reduced.

Further, the present invention provides a method for producing an adhesive patch for the treatment of tinea unguium in which side effects are reduced, the adhesive patch including a backing and a pressure sensitive adhesive layer arranged on at least one side of the backing, the method comprising:

adding terbinafine and/or a pharmacologically acceptable salt thereof in an amount of 3 mg/cm$^2$ to the pressure sensitive adhesive layer; and formulating the adhesive patch so that, when the adhesive patch having an size of 1 cm$^2$ is used so as to be applied to nails once a day, a terbinafine concentration in the nails may be 295±127 ng/mg and a terbinafine concentration in plasma may be 23 pg/mL or less, 8 weeks after the start of application.

Furthermore, the present invention can also be called a side effect-reducing method of an adhesive patch for the treatment of tinea unguium, the adhesive patch including a backing and a pressure sensitive adhesive layer arranged on at least one side of the backing, the method comprising: adding terbinafine and/or a pharmacologically acceptable salt in an amount of 3 mg/cm$^2$ to the pressure sensitive adhesive layer; and formulating the adhesive patch so that, when the adhesive patch having an size of 1 cm$^2$ is used so as to be applied to nails once a day, a terbinafine concentration in the nails may be 295±127 ng/mg and a terbinafine concentration in plasma may be 23 pg/mL or less, 8 weeks after the start of application.

Effects of the Invention

According to the adhesive patch for the treatment of tinea unguium of the present invention, terbinafine having a concentration significantly higher than oral formulations can be transferred to nails, and a very low terbinafine concentration in plasma can be achieved. Further, the therapeutic effect of tinea unguium can be improved than before, and at the same time, side effects such as hepatopathy caused by terbinafine can be suppressed to the minimum, by applying the adhesive patch for the treatment of tinea unguium of the present invention to tinea unguium.

BRIEF DESCRIPTION OF THE DRAWING

FIG. 1 is a graph showing the permeation amount into nails of terbinafine when dose regimen of the adhesive patch for nails according to an embodiment is changed.

EMBODIMENTS FOR CARRYING OUT THE INVENTION

The adhesive patch for the treatment of tinea unguium of the present invention (hereinafter, also referred to as the "adhesive patch for nails") contains 3 mg of terbinafine and/or a pharmacologically acceptable salt thereof per cm$^2$ of a surface perpendicular to the thickness direction, is used so as to be applied to nails once a day, and is used so that the terbinafine concentration in nails may be 295±127 ng/mg and the terbinafine concentration in plasma may be 23 pg/mL or less, 8 weeks after the start of application.

The adhesive patch for nails of the present invention contains terbinafine and/or a pharmacologically acceptable salt thereof in an amount of 3 mg/cm$^2$ and is used so as to be applied to nails once a day. Thus, by applying the adhesive patch for nails once a day, terbinafine can be efficiently transferred from the adhesive patch for nails into nails and accumulated in the nails. Thereby, the terbinafine concentration in nails reaches a steady state in 8 weeks at the latest at a sufficiently high concentration (about 380 times the terbinafine concentration in nails in the case of oral formulations), and after that, the concentration is maintained at this level, thereby capable of obtaining an extremely high therapeutic effect.

As the reason why the adhesive patch for nails of the present invention can achieve a high terbinafine concentration in nails and a low terbinafine concentration in plasma at the same time, it is assumed that the adhesive patch for nails holding terbinafine and/or a pharmacologically acceptable salt thereof in a large amount per unit size is applied by a way of using terbinafine once a day. Terbinafine has a relatively high lipid-solubility, has high compatibility with keratin protein in nails, and is easily transferred into nails and accumulated in the nails. Further, the plasma concentration is suppressed at a low level probably because, in nails, most of terbinafine is present in a state where it is combined with keratin protein, and as a result, the concentration of free terbinafine that participates in the transfer from nails to blood is decreased to reduce the transfer to blood.

In the present specification, the terbinafine concentration in nails means a terbinafine concentration in nails determined by measuring, by LC/MS/MS, the amount of terbinafine extracted from a nail sample ground from a nail upper surface to which the adhesive patch for nails has been applied. Note that the nail sample may be obtained from the human-derived nails used for the nail permeation study or may be obtained directly from humans. Note that the terbinafine concentration in plasma means a terbinafine concentration in plasma obtained from the blood taken from humans.

Here, the nail permeation study refers to a study in which human-derived nails are formed into small square pieces several millimeters square; the circumference thereof is caulked with a silicone sheet and a silicone bond; the upper and lower sides of the nail are sandwiched between silicone O-rings; the nail with O-rings is mounted in an apparatus main body obtained by processing a Cryo-tube; a receiver solution (bovine serum-containing phosphate-buffered saline) is added to the tube; and a predetermined adhesive patch for nails is applied to the nail upper surface in accordance with a predetermined way of using in a state where the receiver solution is held at 32° C.

Terbinafine and/or a pharmacologically acceptable salt thereof contained in the adhesive patch for nails of the present invention includes terbinafine (free body) and a pharmacologically acceptable salt of terbinafine, and examples of the pharmacologically acceptable salt of terbinafine include hydrochloride, sulfate, bromide, mesilate, citrate, fumarate, tartrate, maleate, and acetate of terbinafine. Among these, terbinafine hydrochloride is particularly preferably used.

The adhesive patch for the treatment of tinea unguium according to an embodiment of the present invention includes a backing and a pressure sensitive adhesive layer arranged on at least one side of the backing, and terbinafine and/or a pharmacologically acceptable salt is contained in the pressure sensitive adhesive layer in an amount of 3 mg/cm$^2$. Further, a release sheet to be released in use may be further laminated on the pressure sensitive adhesive layer.

The backing may be that used for a common adhesive patch and is, but not particularly limited to, desirably one that does not influence the release of terbinafine which is contained in the pressure sensitive adhesive layer at a relatively high content. Specific examples which can be used include films or sheets of polyethylene, polypropylene, polybutadiene, an ethylene-vinyl acetate copolymer, polyvinyl chloride, polyester, nylon (registered trademark), polyurethane and the like; laminates thereof; and composite materials thereof. Especially, polyethylene, an ethylene-vinyl acetate copolymer, and polyester are preferably used in terms of a fitting feeling during application to nails and the influence to drug-release properties. Both elastic and nonelastic backings can be used, but elastic backings are preferred in terms of adhesion properties.

Further, in order to increase the absorption of drugs from nails, a backing having a low moisture permeability is preferred.

In the pressure sensitive adhesive layer, at least terbinafine and/or a pharmacologically acceptable salt thereof and an adhesive base agent are contained. Note that, in order to prevent coloring to nails and discoloration of nails, it is preferred not to use a volatile solvent for the pressure sensitive adhesive layer.

The content of terbinafine and/or a pharmacologically acceptable salt thereof in the pressure sensitive adhesive layer may be 3 mg per $cm^2$ of a surface perpendicular to the thickness direction of the pressure sensitive adhesive layer. Note that, it is expected that the same effect will be generated when terbinafine and/or a pharmacologically acceptable salt thereof is contained in an amount in the range of 0.5 to 25 mg per $cm^2$ of a surface perpendicular to the thickness direction of the pressure sensitive adhesive layer.

Further, on condition that the above content is followed, the content of terbinafine and/or a pharmacologically acceptable salt thereof relative to the total mass of the pressure sensitive adhesive layer is preferably 0.5 to 50 mass %, more preferably 10 to 40 mass %, most preferably 20 to 35 mass %. If the content of terbinafine and/or a pharmacologically acceptable salt thereof relative to the total mass of the pressure sensitive adhesive layer exceeds 50 mass %, the physical properties of the adhesive patch will tend to be adversely affected; and if the content is less than 0.5 mass %, there is a tendency that it is impossible to deliver a sufficient amount of terbinafine to exhibit a therapeutic effect.

It is preferred to allow a pressure sensitive adhesive layer to contain sodium acetate together with terbinafine and/or a pharmacologically acceptable salt thereof. By allowing sodium acetate to be contained, it is possible to dissolve terbinafine and/or a pharmacologically acceptable salt thereof in an adhesive base agent at a high concentration, and it is possible to increase the permeability of terbinafine into nails. The content of sodium acetate is preferably 0.5 to 30 mass %, more preferably 1 to 20 mass % relative to the total mass of the pressure sensitive adhesive layer.

The pressure sensitive adhesive component forming the adhesive base agent includes an acrylic pressure sensitive adhesive, a rubber pressure sensitive adhesive, and a silicone pressure sensitive adhesive, and among them, an acrylic pressure sensitive adhesive is preferably used.

The acrylic pressure sensitive adhesive is not particularly limited as long as it is a polymer or a copolymer containing at least one (meth)acrylic acid derivative represented by 2-ethylhexyl acrylate, methyl acrylate, butyl acrylate, hydroxyethyl acrylate, 2-ethylhexyl methacrylate, and the like; and examples which can be used include pressure sensitive adhesives such as an acrylic acid/2-ethylhexyl acrylate/vinyl acetate copolymer, an acrylic acid/octyl acrylate copolymer, a 2-ethylhexyl acrylate/vinyl pyrrolidone copolymer solution, an acrylate/vinyl acetate copolymer, a 2-ethylhexyl acrylate/2-ethylhexyl methacrylate/dodecyl methacrylate copolymer, a methyl acrylate/2-ethylhexyl acrylate copolymer resin emulsion, an acrylic polymer contained in alkanolamine solution of an acrylic resin, which are listed as pressure-sensitive adhesives in Japanese Pharmaceutical Excipients Directory 2007 (edited by Japan Pharmaceutical Excipients Council), Eudragit series (Evonik Industries), and DURO-TAK acrylic pressure-sensitive adhesive series (Henkel Corporation). Further, among them, a pressure sensitive adhesive comprising an acrylic copolymer having a hydroxy group or a carboxylic acid group can be preferably used in terms of adhesiveness to nails and terbinafine-releasing properties. Here, the acrylic pressure sensitive adhesive having a hydroxy group or a carboxylic acid group refers to a compound showing adhesiveness which is a copolymer of two or more (meth)acryloyl monomers (refers to monomers each containing a (meth)acryloyl group) and has a hydroxy group or a carboxyl group, or a copolymer of a (meth)acryloyl monomer and a monomer having an ethylenic unsaturated group (except a (meth)acryloyl monomer) and has a hydroxy group or a carboxyl group.

It is also possible to allow a rubber component of the rubber pressure sensitive adhesive or polysiloxanes of the silicone pressure sensitive adhesive to be contained in the above acrylic pressure sensitive adhesive, and examples of such a rubber component include natural rubber, styrene-butadiene rubber, a styrene-isoprene-styrene block copolymer (SIS), a styrene-butadiene-styrene block copolymer, polyisobutylene (PIB), polyisoprene, and butyl rubber. Among these, it is preferred to use at least one selected from natural rubber, a styrene-isoprene-styrene block copolymer, polyisobutylene, and polyisoprene in terms of the ease of a quality design and the cost.

The mass of the adhesive base agent is preferably 5 to 85 mass %, more preferably 10 to 80 mass %, most preferably 20 to 60 mass % relative to the total mass of the pressure sensitive adhesive layer.

The pressure sensitive adhesive layer may further contain a plasticizer. Examples of the plasticizer which can be used include petroleum-based oils such as paraffin-based process oil, naphthene-based process oil, and aromatic process oil; squalane and squalene; plant oils such as olive oil, camellia oil, castor oil, tall oil, and peanut oil; silicon oil; dibasic acid esters such as dibutyl phthalate and dioctyl phthalate; liquid rubbers such as polybutene and liquid isoprene rubber; liquid fatty acid esters such as isopropyl myristate, hexyl laurate, diethyl sebacate, and diisopropyl sebacate; and diethylene glycol, polyethylene glycol, glycol salicylate, propylene glycol, dipropylene glycol, triacetin, triethyl citrate, and crotamiton. Particularly, liquid paraffin, liquid polybutene, isopropyl myristate, diethyl sebacate, and hexyl laurate are preferred.

The pressure sensitive adhesive layer can contain a tackifier, an absorption enhancer, an antioxidant, an ultraviolet absorber, pigment, a crosslinking agent, a filler, and a preservative as an optional component in addition to the above components.

Examples of the tackifier include rosin and rosin derivatives such as rosin glycerin ester, hydrogenated rosin, hydrogenated rosin glycerin ester, and rosin pentaerythritol ester; alicyclic saturated hydrocarbon resins such as Arkon P-100 (Arakawa Chemical Industries, Ltd.); aliphatic hydrocarbon resins such as Quintone B 170 (Zeon Corporation); terpene resins such as Clearon P-125 (Yasuhara Chemical Co., Ltd.); and maleic acid resins.

Examples of the absorption enhancers include fatty acid, fatty alcohol, fatty acid esters, amides, or ethers, aromatic organic acids, aromatic alcohol, aromatic organic acid esters or ethers having 6 to 20 carbon atoms (all of which may be saturated or unsaturated and may be in a cyclic, linear, or branched form) and further include lactates, acetates, monoterpene compounds, sesquiterpene compounds, Azone, Azone derivatives, pirotiodecane, glycerin fatty acid esters, propylene glycol fatty acid esters, sorbitan fatty acid esters (Span type), polysorbate (Tween type), polyethylene glycol fatty acid esters, polyoxyethylene hydrogenated castor oil (HCO type), polyoxyethylene alkyl ethers, sucrose fatty acid esters, and plant oils.

Specifically, the absorption enhancers are preferably caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, methyl laurate, hexyl laurate, lauric acid diethanolamide, isopropyl myristate, myristyl myristate, octyldodecyl myristate, cetyl palmitate, salicylic acid, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, l-menthol, borneol, d-limonene, isoeugenol, isoborneol, nerol, dl-camphor, glycerin monocaprylate, glycerin monocaprate, glycerin monolaurate, glycerin monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, HCO-60, pirotiodecane, and olive oil; and the absorption enhancers are particularly preferably lauryl alcohol, isostearyl alcohol, lauric acid diethanolamide, glycerin monocaprylate, glycerin monocaprate, glycerin monooleate, sorbitan monolaurate, propylene glycol monolaurate, polyoxyethylene lauryl ether, and pyrrothiodecane.

Examples of the antioxidants include tocopherol and ester derivatives thereof, ascorbic acid, ascorbyl stearate, nordihydroguaiaretic acid, dibutylhydroxytoluene (BHT), and butylhydroxyanisole.

The ultraviolet absorbers preferably include p-aminobenzoic acid derivatives, anthranilic acid derivatives, salicylic acid derivatives, coumarin derivatives, amino acid compounds, imidazoline derivatives, pyrimidine derivatives, and dioxane derivatives.

Examples of the pigment include Red No. 2 (Amaranth), Red No. 3 (Erythrosine), Red No. 102 (New Coccine), Red No. 104 (1), (Phloxine B), Red No. 105 (1) (Rose Bengal), Red No. 106 (Acid Red) 106, Yellow No. 4 (Tartrazine), Yellow No. 5 (Sunset Yellow FCF), Green No. 3 (Fast Green FCF), Blue No. 1 (Brilliant Blue FCF), and Blue No. 2 (Indigocarmine).

The crosslinking agents preferably include thermosetting resins such as amino resins, phenol resins, epoxy resins, alkyd resins, and unsaturated polyester, isocyanate compounds, block isocyanate compounds, organic crosslinking agents, and inorganic crosslinking agents such as metals or metal compounds.

The fillers preferably include calcium carbonate, magnesium carbonate, silicate such as aluminum silicate and magnesium silicate, silicic acid, barium sulfate, calcium sulfate, calcium zincate, zinc oxide, and titanium oxide.

The preservatives preferably include ethyl parahydroxybenzoate, propyl parahydroxybenzoate, and butyl parahydroxybenzoate.

In the adhesive patch for nails, it is preferred that the pressure sensitive adhesive layer is protected by a release sheet before use, that is, during storage thereof, and the release sheet is released before the adhesive patch for nails is used. The release sheet is not particularly limited as long as it is generally used for adhesive patches, but polyethylene, polypropylene, and polyester to which release treatment has been applied are preferably used. These release sheets are preferably those in which silicone treatment has been applied to the surface to be brought into contact with the pressure sensitive adhesive layer, as the release treatment. By applying the silicone treatment, the release sheet can be easily removed from the pressure sensitive adhesive layer at the time of use.

Next, a method for producing the adhesive patch for nails according to an embodiment of the present invention will be described.

Examples of the method for producing the adhesive patch for nails according to the present embodiment include a method comprising: thermally melting the adhesive base agent, terbinafine and/or a pharmacologically acceptable salt thereof, and other components as described above; applying the melt to a release sheet or a backing; and then laminating the resulting release sheet or the backing with a backing or a release sheet, respectively.

An alternative method comprises: dissolving or uniformly dispersing in a solvent the adhesive base agent, terbinafine and/or a pharmacologically acceptable salt thereof, and other components as described above to prepare a coating liquid for forming an adhesive layer; spreading the coating liquid on a release sheet or a backing to dry and remove the solvent; and then laminating the resulting release sheet or the backing with a backing or a release sheet, respectively. Another alternative method comprises: uniformly applying the above coating liquid for forming an adhesive layer to a release sheet; removing the solvent of the coating film to form a pressure sensitive adhesive layer; and then laminating a backing to the release sheet.

A well-known solvent can be used as the solvent, and examples include toluene, xylene, hexane, cyclohexane, ethyl acetate, and propyl acetate. Especially, toluene, hexane, and ethyl acetate are preferred.

With respect to the drying conditions for removing the solvent of the coating film, it is preferred that the drying is performed at 60 to 100° C. for about 2 to 20 minutes.

The thickness of the pressure sensitive adhesive layer is not limited as long as it can contain terbinafine and/or a pharmacologically acceptable salt thereof in an amount of 3 mg/cm$^2$, but the thickness is generally 50 to 500 µm, preferably 50 to 300 µm. Further, the size of a surface perpendicular to the thickness direction of the pressure sensitive adhesive layer, that is, the size of the adhesive patch for nails, may be an size that is large enough to cover the surface of a nail plate, optionally including the skin around the nail, and is generally 0.5 to 10 cm$^2$, preferably 0.5 to 5 cm$^2$, more preferably 1 to 4 cm$^2$. The shape of the adhesive patch for nails can be arbitrarily set to circular, elliptical, square, rectangular, or other shapes. Among these, a rectangular shape is particularly preferred because it fits in the shape of a nail (particularly root part). Further, from the point of view of improving the handleability and the feeling of application, even a square or rectangular shape is preferably a shape in which the corners are rounded.

The present invention may also be an administration method of applying an adhesive patch for the treatment of tinea unguium to nails once a day, the adhesive patch comprising terbinafine and/or a pharmacologically acceptable salt thereof in an amount of 3 mg/cm$^2$, wherein the terbinafine concentration in nails is 295±127 ng/mg and the terbinafine concentration in plasma is 23 pg/mL or less, 8 weeks after the start of application, per cm$^2$ of the adhesive patch.

According to this administration method, a steady state is reached earlier than in the case where terbinafine and/or a pharmacologically acceptable salt thereof are orally administered; a significantly high concentration of terbinafine can be transferred to nails; and a very low terbinafine concentration in plasma can be achieved. Further, the therapeutic effect of tinea unguium can be improved compared with conventional methods, and at the same time, side effects such as hepatopathy caused by terbinafine can be suppressed to the minimum. Furthermore, since the administration method according to the present embodiment depends on the application of the adhesive patch on nails, administration is simple, and in addition, a use feeling is improved compared with external preparations other than the adhesive patch.

The present invention may also be a therapeutic method of tinea unguium including applying an adhesive patch for the treatment of tinea unguium to nails once a day, the adhesive patch comprising terbinafine and/or a pharmacologically acceptable salt thereof in an amount of 3 mg/cm$^2$, wherein the terbinafine concentration in nails is 295±127 ng/mg and the terbinafine concentration in plasma is 23 pg/mL or less, 8 weeks after the start of application, per cm$^2$ of the adhesive patch.

EXAMPLES

Hereinafter, the present invention will be described more specifically with reference to Examples, but the present invention is not intended to be limited to these Examples, and various changes or modifications can be made without departing from the technical principles of the present invention.

Examples 1 to 10

Adhesive patches for nails having the compositions shown in Table 1 were produced. In Table 1, the acrylic pressure sensitive adhesive is an acrylic acid/2-ethylhexyl acrylate/vinyl acetate copolymer (acrylic acid-2-ethylhexyl acrylate-vinyl acetate copolymer). Specifically, terbinafine hydrochloride, terbinafine, sodium acetate, and sorbitan fatty acid ester were put in a mortar and well mixed in advance so that the mixture may have the composition shown in Table 1, and the resulting mixture was mixed with the acrylic pressure sensitive adhesive dissolved in ethyl acetate. The resulting mixture was applied to a release sheet and then ethyl acetate as a solvent was removed by drying, and the resulting release sheet was bonded with a PET film backing, thus obtaining an adhesive patch for nails (containing 3 mg/cm$^2$ of terbinafine hydrochloride). The size (cm$^2$) and shape of the adhesive patch for nails of each Example are shown in Table 1.

TABLE 1

Composition of adhesive patch for nails

| Components | Example 1 | Example 2 | Example 3 | Example 4 | Example 5 | Example 6 | Example 7 | Example 8 | Example 9 | Example 10 |
|---|---|---|---|---|---|---|---|---|---|---|
| Terbinafine hydrochloride | 30 | 30 | 30 | 30 | 30 | 20 | 20 | — | — | — |
| Terbinafine | — | — | — | — | — | — | — | 30 | 30 | 30 |
| Acrylic pressure sensitive adhesive | 45 | 52 | 52 | 52 | 52 | 65 | 65 | 65 | 65 | 65 |
| Sodium acetate | 20 | 15 | 15 | 15 | 15 | 10 | 10 | — | — | — |
| Sorbitan fatty acid ester | 5 | 3 | 3 | 3 | 3 | 5 | 5 | 5 | 5 | 5 |
| Size of adhesive patch for nails (cm$^2$) | 1 | 1 | 1 | 4 | 6 | 1 | 4 | 1 | 4 | 6 |
| Shape of adhesive patch for nails | Elliptical | Elliptical | Rectangular | Rectangular | Rectangular | Elliptical | Rectangular | Elliptical | Rectangular | Rectangular |

*The unit of each composition is "mass %".

(Performance Evaluation of the Adhesive Patch for Nails)

1. In Vitro Evaluation

<Method>

The nails provided by adult men and women were formed into small square pieces several millimeters square, and the circumference thereof was caulked with a silicone sheet and a silicone bond. The upper and lower sides of the nail were sandwiched between silicone O-rings, and the nail with O-rings was mounted in a nail permeation apparatus obtained by processing a Cryo-tube. A receiver solution (bovine serum albumin-containing phosphate-buffered saline) in an amount of 1 mL was added to the lower surface side of the nail in the tube, and the adhesive patch for nails obtained in Example 2 was cut into a square of 3 mm×3 mm and applied to the upper surface of the nail. The adhesive patch for nails was successively applied for 4 weeks, 8 weeks, 12 weeks, and 16 weeks while holding the receiver solution at 32° C. and newly replacing the adhesive patch for nails once a day (a 4-week application group, an 8-week application group, a 12-week application group and a 16-week application group, respectively, 4 groups in total, n=9 for each group). The adhesive patch for nails was removed, and then a nail sample collected by grinding from the upper layer part of the nail (the surface to which the adhesive patch for nails was applied) was used for the measurement of the terbinafine concentration in nails. The terbinafine concentration in nails was calculated by measuring the amount of the drug extracted from the nail sample by LC/MS/MS.

<Results>

The results of the measurement of the terbinafine concentration in nails are shown in Table 2. The average values of the terbinafine concentration in nails were 117, 295, 286, and 233 ng/mg for the 4-week application group, the 8-week application group, the 12-week application group, and the 16-week application group, respectively (Table 2). Further, the standard deviations were 70, 127, 112, and 68 ng/mg, respectively (Table 2). The terbinafine concentration in nails had reached a steady state about 8 weeks after the start of application.

TABLE 2

Terbinafine concentration in nails

| Period of application (weeks) | Terbinafine concentration in nails (ng/mg) | |
|---|---|---|
| | Average value | Standard deviation |
| 4 | 117 | 70 |
| 8 | 295 | 127 |
| 12 | 286 | 112 |
| 16 | 233 | 68 |

2. Study of Applying Method

<Method>

The amount of terbinafine that permeates nails in the case where the adhesive patch for nails obtained in Example 2 was newly replaced every day was compared with that in the case where the same was newly replaced every week. In the same manner as in the in vitro evaluation, the adhesive patch for nails obtained in Example 2 was applied to the human nail; the receiver solution was collected every week; the terbinafine concentration in the receiver solution was measured by LC/MS/MS; and the resulting concentration was defined as the concentration in permeation solution (ng/mL). For comparison, the measurement was performed also in the case where the patch was applied once for 24 hours and the case where the patch was continuously applied without newly replacing.

<Results>

The results of the measurement are shown in FIG. 1. The abscissa of FIG. 1 shows the days elapsed from the start of application, and the ordinate shows the concentration in permeation solution. The rising ratio of the concentration in permeation solution in the case where the patch was continuously applied was larger than that in the case where the patch was applied once for 24 hours, and the rising ratio in the case where the patch was newly replaced every week was much larger than those in the former cases. Further, the rising ratio in the case where the patch was newly replaced every day was much larger than that in the case where the patch was newly replaced every week (FIG. 1). From these results, it was assumed that the concentration in the lower layer of nails can be increased more quickly by newly replacing the patch every day.

3. Clinical Study to Tinea Unguium Patient

<Method>

The adhesive patches for nails obtained in Example 2 cut so that each may have a patch size of 1 cm² were applied to the first toe nails of tinea unguium patients (71 subjects), and the patches for nails were repeatedly applied for 24 weeks while newly replacing the patches for nails once a day. 2 Weeks, 8 weeks, and 24 weeks after the start of application, the patient's blood was collected to measure the terbinafine concentration in plasma. Further, 8 weeks and 24 weeks after the start of application, the nail boundary proximal part, the nail separation part (opaque part), and the nail separation part (non-opaque part) were collected to measure the terbinafine concentration in nails. LC/MS/MS was used for the measurement of terbinafine concentration.

TABLE 3

Terbinafine concentration in plasma of tinea unguium patient
Terbinafine concentration in plasma (pg/mL)

| Period of application | Average value | Standard deviation |
|---|---|---|
| 2 weeks | 6.1 | 4.3 |
| 8 weeks | 10.2 | 12.8 |
| 24 weeks | 11.3 | 15.8 |

TABLE 4

Terbinafine concentration in nails of tinea unguium patient
Terbinafine concentration in nails (ng/mg) (median)

| Period of application | Boundary proximal part | Nail separation part (opaque part) | Nail separation part (non-opaque part) |
|---|---|---|---|
| 8 weeks | 148 | 149 | 44.5 |
| 24 weeks | 221 | 224 | 88.7 |

<Results>

Table 3 shows the measurement results of terbinafine concentration in plasma 2 weeks, 8 weeks, and 24 weeks after the start of application. The terbinafine concentration in plasma reached almost a steady state 8 weeks after the start of application, and the concentration at this time was 10.2±12.8 pg/mL in average.

Table 4 shows the measurement results of terbinafine concentration in nails 8 weeks and 24 weeks after the start of application. Note that the terbinafine concentration in nails was evaluated using a median because the variation in the results of measurement in each collection part was large and the possibility of contamination was suggested, in the evaluation of the terbinafine concentration in nails. As a result, it was estimated that almost a steady state was reached 8 weeks after the start of application, showing the same tendency as in the results in the in vitro evaluation. Further, any side effect derived from terbinafine was not observed during the clinical study.

The invention claimed is:

1. An adhesive patch for the treatment of tinea unguium intended to be applied once a day, comprising terbinafine and/or a pharmacologically acceptable salt thereof in an amount of 3 mg/cm²,
    wherein the adhesive patch is capable of dosing a terbinafine concentration in nails of 295±127 ng/mg and a terbinafine concentration in plasma of 23 pg/mL or less, 8 weeks after the start of application, per cm² of the patch size.

2. A method for producing an adhesive patch for the treatment of tinea unguium in which side effects are reduced, the adhesive patch comprising a backing and a pressure sensitive adhesive layer arranged on at least one side of the backing, the method comprising:
    adding terbinafine and/or a pharmacologically acceptable salt thereof in an amount of 3 mg/cm² to the pressure sensitive adhesive layer; and
    formulating the adhesive patch so that, when the adhesive patch having size of 1 cm² is used so as to be applied to nails once a day, the patch is capable of dosing a terbinafine concentration in the nails of 295±127 ng/mg and a terbinafine concentration in plasma of 23 pg/mL or less, 8 weeks after the start of application.

3. A method of reducing side effects in a patient in the treatment of tinea unguium comprising administering to a patient in need thereof an adhesive patch comprising terbinafine and/or a pharmacologically acceptable salt thereof in an amount of 3 mg/cm$^2$, wherein the adhesive patch is applied once per day, and wherein the adhesive patch is capable of dosing a terbinafine concentration in nails of 295±127 ng/mg and a terbinafine concentration in plasma of 23 pg/mL or less, 8 weeks after the start of application, per cm$^2$ of the patch size.

* * * * *